United States Patent [19]

Friesch

[11] Patent Number: 5,064,492

[45] Date of Patent: Nov. 12, 1991

[54] METHOD FOR PRODUCING DISPOSABLE GARMENT

[76] Inventor: Andrew J. Friesch, W73 N1030 Poplar Ave., Cedarburg, Wis. 53012

[21] Appl. No.: 416,041

[22] Filed: Oct. 3, 1989

[51] Int. Cl.$^5$ .............................................. B32B 31/00
[52] U.S. Cl. .................................. 156/191; 156/277; 156/291; 156/292; 156/320; 156/324; 156/324.4; 427/177; 427/208.2; 604/365; 604/366
[58] Field of Search ............... 156/191, 320, 277, 324, 156/291, 292, 324.4; 427/177, 208.2; 604/365, 366

[56] References Cited

U.S. PATENT DOCUMENTS

| | | | |
|---|---|---|---|
| 4,147,580 | 4/1979 | Buell | 156/291 |
| 4,526,577 | 7/1985 | Schmidt et al. | 156/291 |
| 4,911,948 | 3/1990 | McIntyre | 427/208.2 |

Primary Examiner—John J. Gallagher
Attorney, Agent, or Firm—Whyte & Hirschboeck

[57] ABSTRACT

An improved disposable garment is manufactured using a moisture impermeable film which is preprinted with an adhesive that is nonblocking at temperatures up to about 110° F. Film so coated can be rewound onto itself and later used with nonwoven material and absorbent pads to produce disposable garments. The preprinted adhesive is heat activated during production of the garments immediately prior to bonding to the nonwoven material and absorbent pads. Delays in manufacture due to clogging of adhesive and inconsistent amounts of adhesive are avoided and considerably less adhesive material is used per garment. Once the adhesive is heat activated and comes into contact with the absorbent pads and nonwoven material, compressing ensures a strong bond between the materials used in the garment.

11 Claims, 2 Drawing Sheets

METHOD FOR PRODUCING DISPOSABLE GARMENT

BACKGROUND OF THE INVENTION

1. Field of the Invention

The present invention relates generally to disposable garments such as diapers and incontinent pad type garments More particularly, the present invention relates to an improvement in the composition of adhesives used to bond nonwoven material and an impermeable film in such garments. Further, the present invention relates to a method for producing such improved garments.

2. Description of the Related Art

Disposable garments such as diapers and incontinent pad type garments usually comprise a moisture impermeable outer film, an intermediate absorbent pad and a moisture permeable inner liner commonly called "nonwoven" material. Disposable garments are typically bonded together utilizing a hot melt adhesive either extruded or sprayed onto the film and/or nonwoven material. This conventional product and assembly method suffers from a number of shortcomings.

Adhesives presently used for bonding garments together include those generally referred to as pressure and semi-pressure sensitive adhesives. Examples of polymers used in present adhesive compositions are styrene-isoprene-styrene, styrene-butadiene-styrene, amorphous polypropylene and ethylene vinyl acetate. These polymers are blended with any of a variety of tackifying resins to impart tack to the hot melt at room temperature. Additional additives are used to modify viscosity and give heat stability.

The adhesive is either extruded in multiline form or sprayed onto the impermeable film. In either case, direct application on the garment production line is labor intensive. Monitoring and close control of application conditions are needed to assure adequate product quality and quantity. Approximately 0.9 gram to 1.5 grams of adhesive is required per garment in order to bond the impermeable film to the nonwoven backing.

Hot melt adhesives have undesirable characteristics when used in connection with these products. Such adhesives are solid at room temperature and become thermoplastic when heated for application. While hot melt pressure and semi-pressure sensitive adhesives effectively bond garments when correctly applied, they do have negative consequences to production, quality and cost of the disposable product. The film to which the high temperature thermoplastic material is applied can be distorted by the elevated temperature. Likewise, a cooling period is required after application and bonding of the film and nonwoven material. Furthermore, the application of multiple beads of melted adhesive in a high speed production line complicates the manufacture and maintenance of high quality standards and, as a result, the ultimate quality of the finished product.

An improvement in the adhesive composition which would avoid the above-mentioned problems and could be used in a high speed, efficient manufacturing system, would prove to be a significant advancement in the art.

FIG. 1 is provided to illustrate a schematic of a conventional prior art system for producing disposable garments. In FIG. 1, a roll 20 supplies a moisture impermeable web or film 22 to produce garments. The garments also comprise an interliner web of absorbent or permeable nonwoven material 24 and individual absorbent pads 26. The film or web 22, the web of nonwoven material 24 and absorbent pads 26 move in a direction indicated by arrows 28. An adhesive applicator station 30 includes one or more nozzles 32 for applying the adhesive to the film 22. After application of the adhesive, the material's are pressure bonded together by means of nip rolls 34, and thereafter separated into individual garments by means of a conventional slitting and/or transverse cutting operation (not shown).

FIGS. 2A and 2B are also prior art illustrations showing alternative methods conventionally used to apply adhesive. In FIG. 2A, a number of extrusion nozzles 32A apply individual beads of adhesive onto the film 22. Similarly, in FIG. 2B, individual spray nozzles 32B spray a swirl pattern on the film prior to bonding.

Clogging, slow line speed and control of adhesive quantity all present problems in the operation of these earlier systems. A system for producing disposable garments which would avoid the above-mentioned problems and could be used in a high speed efficient manufacturing system, would prove to be a significant advancement in the art.

OBJECTS AND SUMMARY OF THE INVENTION

It is one object of the present invention to eliminate direct on-line application of hot melt adhesives in the production of disposable garments.

It is another object of the present invention to provide a method for producing a disposable garment which significantly reduces slowdowns in production, and labor intensive monitoring and control steps, due to the application of adhesives.

It is yet another object of the present invention to provide a disposable garment product which uses significantly less adhesive than earlier products.

It is a further object of the present invention to provide a method of producing disposable garment products which does not require high temperatures in the production of the disposable garment product.

A still further object of this invention is to provide a method of precoating an impermeable film or web with a heat-activated adhesive, which method utilizes a simplified heating element, to thereby reduce capital machinery expense and later labor-intense maintenance.

How these and other objects of the present invention are accomplished will be explained in a detailed description of the preferred embodiment of the present invention in connection with the FIGURES. Generally, however, the objects are accomplished using an adhesive to precoat the film. The adhesive is non-blocking at room temperature and does not reach a blocking state until approximately 110° F. (A blocking state is achieved when unwinding of the roll of film is adversely affected by adhesion of adjoining surfaces of the film to one another after the adhesive becomes tacky. That is, blocking occurs when the tension causing the roll to unwind causes damage to the film due to adhesion of the film to itself.) In addition, the adhesive is bondable via print application, or some other means, to a moisture impermeable film during a converting stage prior to product manufacturing. The adhesive bonds permanently to the film when applied in the preconverted stage at a temperature below the distortion temperature of the film.

Thus, film coated with such an adhesive can then be rewound onto itself without concern for blocking. The coated film is converted by the disposable product manufacturer at a later point on the production line. This is accomplished by unwinding the coated film, heat activating the coated area, and nipping the film to the nonwoven and absorbent materials on the production line.

If desired, the adhesive application step and monitoring of said step may therefore be completely eliminated during garment assembly. Because adhesive application is more carefully controlled in the preconverting stage, the amount of adhesive used is significantly less than in prior products.

Other ways in which the objects may be accomplished, all of which are deemed to fall within the scope of the present invention, will be described and will become apparent to those of ordinary skill in the art in the remainder of the specification. The descriptions in the specification are deemed to be illustrative and not limiting, the present invention being limited only by the scope of the claims which follow the detailed description of the preferred embodiment.

DESCRIPTION OF THE DRAWINGS

In the several drawing FIGURES, like reference numerals refer to like components.

DESCRIPTION OF THE PREFERRED EMBODIMENT

Preprinting of Adhesive

Figure 2A:
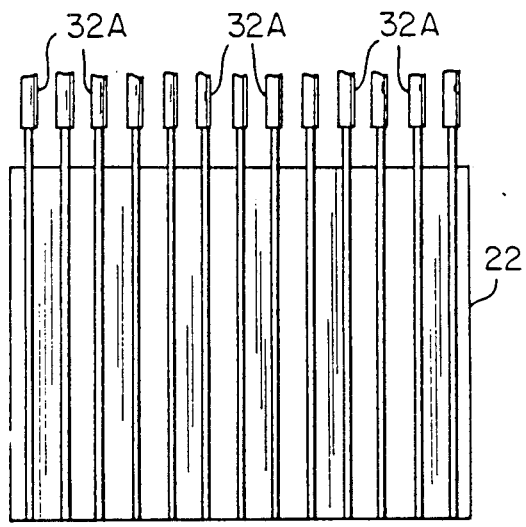
FIG. 2A is a top view of the extrusion glue applicator station used in the prior art system shown in FIG. 1.
Figure 2B:
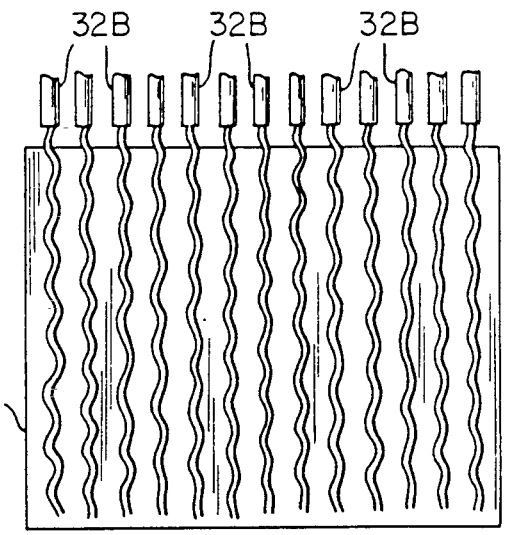
FIG. 2B is a spray nozzle glue applicator alternatively used in the prior art system shown in FIG. 1.
Figure 1:
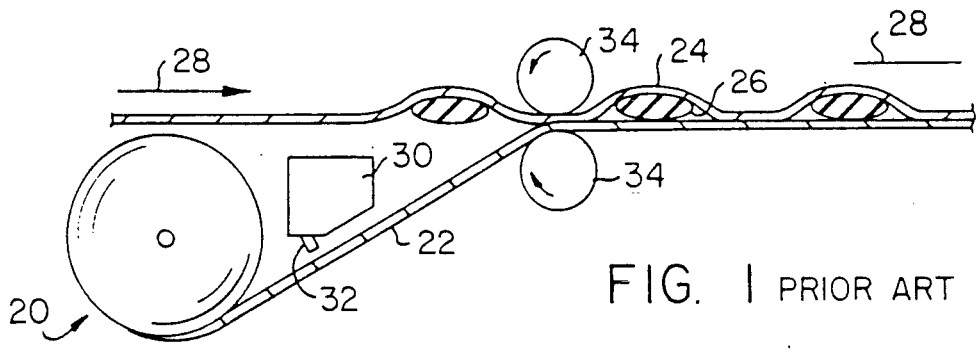
FIG. 1 is a schematic side view of a prior art production line for making disposable garments.
Figure 3:
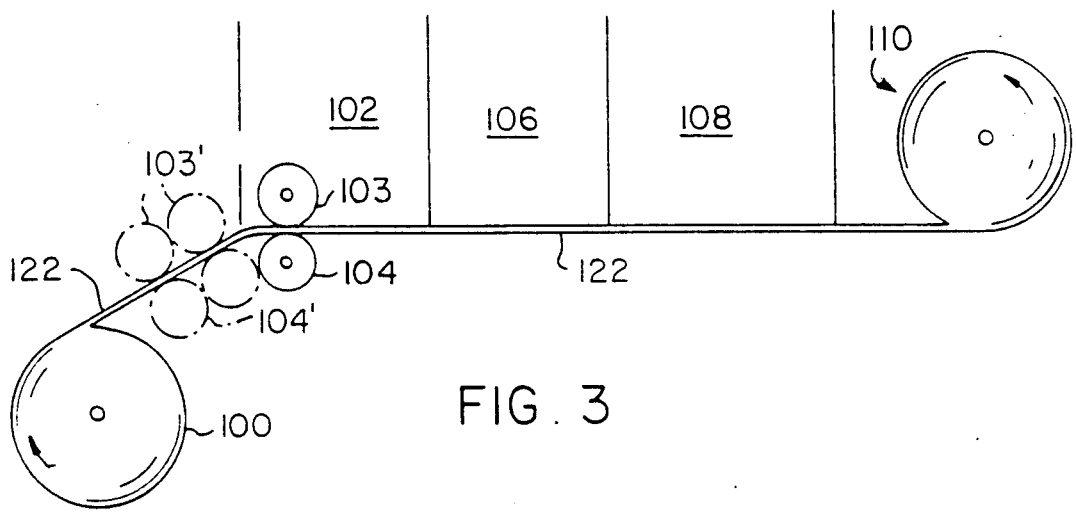
FIG. 3 is a schematic diagram of the preprinting step of the present invention.

FIG. 3 schematically illustrates a system for preprinting adhesive on a surface film rolled to be used to produce disposable garments. A roll 100 supplies a continuous web of film 122 which is preferably moisture impermeable for a preprinting system according to the present invention. The film 122 sequentially encounters a printing section 102, a cooling area 106 and a slitting area 108 (when desired) before being rewound onto a preprinted roll of film 110.

While passing printing section 102, a film 122 has permanently imprinted thereon at elevated temperatures a patterned array of adhesive. A printing or transfer cylinder 103 is a patterned roll which transfer prints adhesive directly to the film 122. In order to maintain proper tension and to assist in cooling the adhesive after application, a chill roll 104 is preferably located directly beneath each printing cylinder 103.

Figure 4:
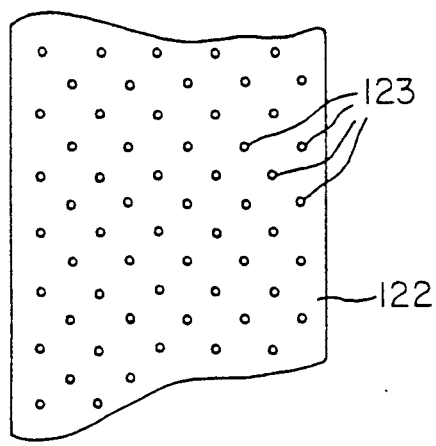
FIG. 4 is a preferred print pattern of moisture impermeable film used in the present invention.

The application of printed patterns 123 of adhesive by means of a printing cylinder 103 is well known to those skilled in the art and will not be discussed in detail. A variety of print patterns 123 can be applied to the film. In FIG. 4 a continuous dot pattern is provided which gives uniform bonding while materially reducing the amount of adhesive (approximately 0.4 gram to 0.9 gram of adhesive per garment). The printed pattern 123 may also be a repeating series of toys, animals, a corporate logo, etc. This repeating pattern can be highlighted by adding a conventional coloring agent such as a dye or pigment to the adhesive composition to make a color pattern more visible through the film.

It should also be noted that more than one printing cylinder may be used. For example, in FIG. 3, second and third printing cylinders 103' and chill rolls 104' are shown in phantom. Multiple print cylinders can increase print speed by allowing simultaneous printing of a number of designs. Use of multiple printing cylinders also permits application of a plurality of distinct designs onto a single roll of film.

After preprinting, the preferred adhesive composition is non-blocking at room temperature and remains non-blocking up to a temperature of about 110° F.

Bonding of Precoated Film on A Disposable Garment Line

Figure 5:
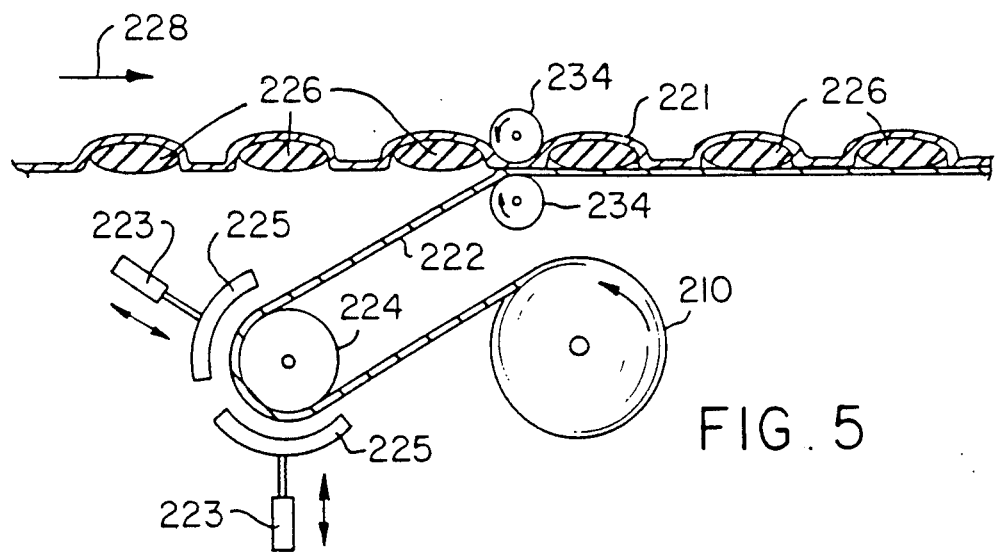
FIG. 5 is a side schematic view of the garment assembly system of the present invention.

FIG. 5 shows a preferred embodiment of an assembly line for producing disposable garments. A preprinted web or film 222, supplied from roll 210 is run over a chill roll 224. The chill roll 224 may also be a tension roll if chilling is not required. Facing the printed pattern side of the film 222 is at least one heater unit 225. Specific location and operation of the heater units 225 will be discussed in greater detail below.

The adhesive is heated so that when it encounters the line of absorbent pads 226 and the nonwoven material 221 moving in the direction indicated by arrow 228, the adhesive is properly melted to permit bonding of the film to the absorbent pads 226 and/or the nonwoven material 221. Bonding is further enhanced by compression rollers 234 located above and below film 222 and the nonwoven material 221. After bonding, the bonded material is cut into individual garments.

As can be seen in FIG. 5, no slowdowns are encountered in the assembly of the garments, since application of an adhesive has been eliminated. Furthermore, monitoring and quality control is minimized. There is no need to check application of adhesive on line to ensure that sufficient, though not excessive, amounts of adhesive are being used and that clogging does not occur. It will be apparent that, if desired, adhesive may be pre-applied on a separate operating line by the manufacturer using printing techniques described herein.

Alternate Assembly Configuration

Figure 6:
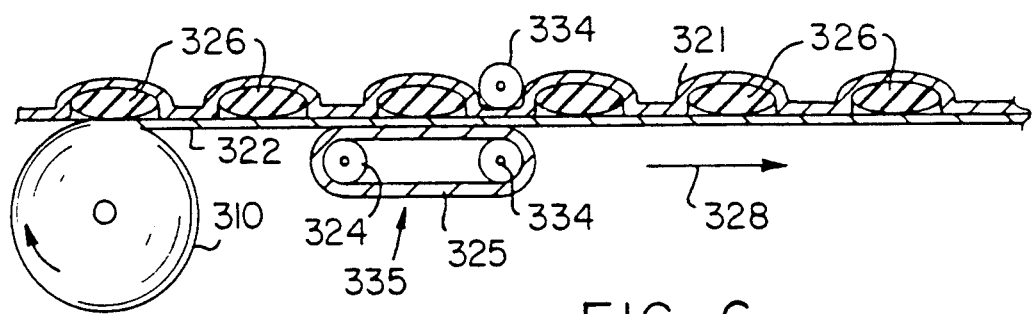
FIG. 6 is an alternative embodiment of the garment assembly system of the present invention.

FIG. 6 shows an alternate configuration for assembly of disposable garments. Continuous nonwoven material 321 and absorbent pads 326 meet the film 322 just as in the preferred system of FIG. 5. Once again, the materials are all moving in the direction of arrows 328. Preprinted film roll 310 supplies film 322 to the system.

In this alternate configuration, however, the compression rollers and heating section have been combined to form a single heating section 335. Compression rollers 334 still work to press the nonwoven material 321, the absorbent pads 326 and the preprinted film 322 together to form garments.

Compression and heating are accomplished by means of an upper compression roller 334, a lower compression roller 334, a lower heated roller 324 and a continuous belt 325 driven by lower rollers 324 and 334. Lower rollers 324 and 334 and heat belt 325 provide a high enough temperature to activate the adhesive on film 322. Rollers 334 then compress the nonwoven material 321, absorbent pad 326 and film 322 at the end of the heat exposure.

Adhesive Composition

The preferred adhesive is non-blocking up to temperatures of up to 110° F. and is low enough in viscosity between 210° F. and 275° F. to allow for preprinting onto film by at least one printing cylinder or other appropriate means. The film is usually made of polyethylene or polypropylene and is conventionally 1.0 to 1.5 mils thick.

The preferred adhesive formula is as follows:
Polymer component:
  25.0% EVA - 28% vinyl acetate content
    - melt index of 400
  30.0% EVA - 28% vinyl acetate content
    - melt index of 800
Tackifying agent:
  44.0% alpha-methyl styrene vinyl toluene monomer hydrocarbon (e.g., Hercules Piccotex LC)
Stabilizer:
  1.0% tetrakis [methylene (3,5-di-tert-butyl-4-hydroxyhydrocinnamate)] methane (e.g., CIBA-GEIGY Irganoz 1010)

Preparation of the preferred adhesive composition involves blending the tackifying resin and anti-oxidant at a temperature above the melting temperature of either material until the mixture is homogeneous. The EVA polymer blend is then added at the same or slightly higher temperature until the blend is homogeneous. When cooled after blending, the resulting mixture is solid and nontacky at ambient temperatures up to approximately The composition is also a free flowing liquid at 210° F. and above. After formulating the above preferred composition, a quantity of the adhesive was coated onto polyethylene film. The bond strength of the coated film, when heat sealed to nonwoven material, was found to be comparable to multi-bead adhesive application presently used in the disposable garment industry.

In the preferred embodiment of the present invention, the adhesive composition contains about 50% or more, by weight, of one or more ethylene vinyl acetate (EVA) thermoplastic polymers. The specific characteristics of the polymer component can be selected by one of ordinary skill in the art of depending on the adhesive's desired properties. Acceptable ethylene vinyl acetate polymers and blends include those having a melt index of approximately 500 or more and a vinyl acetate content of approximately 28% or more. The melt index is determined using ASTM test 1238.

In selecting the base polymer, it is important that the polymer have a low enough viscosity at application temperature to allow for efficient application processing. Application is preferably by a printing cylinder, such as the cylinder 103 shown in FIG. 3. Additionally, the percentage of polymer in the formula must be adequate to obtain sufficient cohesive strength in the bonded area. A low density polyethylene could be employed if it has a high enough melt index to be processable in the system.

The adhesive preferably contains between approximately 30% and 49%, by weight, of a tackifying agent, usually a resin or blends, having a melt point between 85° C. and 105° C. Tackifying agents, such as a modified terpene, glycerol ester of acintol R tall oil resin, or a mixed olefin polymerized petroleum hydrocarbon, may be used instead of those in the above formula. Selection of a substitute agent should be based on that agent's specific adhesion to a selected impermeable film, such as polyethylene or polypropylene. A further consideration in selecting an alternative agent is that the tackifying agent must have a high enough melt point to eliminate concern for blocking due to temperature during storage.

The adhesive can also contain a small amount of a suitable anti-oxidant for stability. The anti-oxidant used will depend on the nature of the composition of other materials. The amount and type of anti-oxidant should be selected taking into consideration the color and physical property stability of the overall formula. A level about 0.2% to 1.0% is usually sufficient to make the formula relatively heat stable as compared to past disposable garment adhesives used. Degradation due to excessive exposure to oxygen and/or excessive or repeated exposure to heat plagues hot melt adhesives. Because of the highly controlled nature of the present process and the use of an anti-oxidant, such degredation does not pose any threat to the integrity of the adhesive.

The preferred heat activation mechanism employed is operated to activate the precoated film at a temperature below the melt point of the impermeable film to avoid film distortion, but at the same time activate the adhesive to form an adequate bond to the nonwoven material. The heater element is preferably automatically controlled to heat the adhesive at varying line speeds.

Because dwell time is important for the adhesive, a moving heating element, as schematically shown in FIG. 5, may be employed. As line speed increases, the heating unit 225 may be moved closer to the film to provide a higher temperature with shorter dwell time to activate the adhesive. At lower line speeds, the heating unit 225 may be moved away from the film allowing for longer dwell time in the proximity of the heat unit, with lower temperatures. A control mechanism, such as a conventional solenoid operated hydraulic piston activator 223 in operable connection with the respective heater unit 225, moves the unit 225 in opposite directions.

The mechanism 223 is controlled by conventional means to laterally move unit 225 away from or closer to the film 222 depending upon the axial speed of the film, materials used or variation in adhesive composition.

Although the heater units 225 and 335 described in connection with the views of FIGS. 5 and 6 have been described in detail, it is within the province of the present invention to provide a combination heat, seal and pressure bonding by means of modification of the compression rollers 234 and 334 respectively. That is, the compression rollers 234, 334 may be supplied with heated, radially extending flange portions at the opposite ends of the roller or in the center slightly spaced from the area enclosing the pad or garment 226. The flanges are heated to provide both compression and heat bonding of the film or web 222 to the pads 226 and/or overlying film of nonwoven material 221. Thus, it will be apparent that the invention contemplates variations in construction to both fit present installations with minimal modification to those installations and to provide versatility in design of new assembly line installations.

Other variations and modifications to the present design will become apparent to one presently of ordinary skill in the art after reading the above specification in connection with the FIGURES. However, the scope of the present invention is to be limited only by the scope of the claims which follow.

What is claimed is:

1. A method for producing a disposable garment having an absorbent pad therein, which comprises the steps of:
   (a) at an elevated temperature preprinting one side of a web of moisture impermeable film with heat activatable adhesive, said adhesive being non-tacky and non-blocking at ambient temperatures and being a free flowing liquid at temperatures of 210° F. and above,
   (b) cooling said web below 110° F.,
   (c) winding said web into a roll,
   (d) unwinding said web from said roll and feeding it to a bonding area
   (e) heat activating said adhesive;
   (f) positioning a plurality of absorbent pads adjacent said preprinted film;
   (g) feeding a web of non-woven material to said bonding area to a position overlying said pads; and
   (h) enclosing said pads by bonding said film to said overlying web of nonwoven material, and
   (i) cutting the resultant bonded materials to form individual garments.

2. The method of claim 1, wherein heat activation is accomplished by a heating unit disposed in the proximity of said film.

3. The method of claim 2, wherein said adhesive is non-tacky up to a temperature of about 110° F.

4. The method of claim 3, wherein said adhesive comprises at least about 50%, by weight, of an ethylene vinyl acetate (EVA) polymer having a melt index of about 500 or more and a vinyl acetate content of at least about 28%.

5. The method of claim 4, wherein said adhesive further comprises between about 30% and 49% by weight, of a tackifying agent having a melt point between about 85° C. and 105° C.

6. The method of claim 5, wherein said adhesive further comprises between about 0.2% and 1.0% of a stabilizer.

7. The method of claim 6, wherein said adhesive has the following formula:
   20.5% EVA having 28% vinyl acetate content and a melt index of 400;
   30.0% EVA having 28% vinyl acetate content and a melt index of 800;
   44.0% alpha-methyl styrene vinyl toluene monomer hydrocarbon; and,
   a minor amount of an anti-oxidant.

8. The method of claim 3, wherein said bonding is accomplished by compressing said nonwoven material and said film concurrently with heat activation of said adhesive.

9. The method of claim 8, wherein said compressing is accomplished by means of a plurality of compression rollers.

10. The method of claim 1, wherein said preprinting is accomplished by at least one printing cylinder which permanently imprints adhesive onto said film.

11. The method of claim 10, wherein said adhesive is printed on said film in a repeating pattern.

* * * * *